United States Patent [19]

Fields: Ellis K. et al.

[11] 4,435,593
[45] Mar. 6, 1984

[54] ADDUCTS OF 1-CYCLOHEXENE-1,2-DICARBOXYLIC ANHYDRIDE WITH OLEFINS

[75] Inventors: Ellis K. Fields, River Forest, Tayseer S. Nimry, Wheaton, both of Ill.

[73] Assignee: Standard Oil Company (Indiana), Chicago, Ill.

[21] Appl. No.: 430,340

[22] Filed: Sep. 30, 1982

Related U.S. Application Data

[62] Division of Ser. No. 330,154, Dec. 14, 1981, Pat. No. 4,371,701.

[51] Int. Cl.$^3$ ............................................. C07C 69/753
[52] U.S. Cl. ................................................... 560/119
[58] Field of Search ............................... 560/117, 119; 204/158 HE

[56] References Cited

PUBLICATIONS

Bloom et al., Journal of the Chemical Society, Chem. Comm., (1972) pp. 96 & 97.

*Primary Examiner*—Richard Raymond
*Attorney, Agent, or Firm*—William C. Clarke; William T. McClain; William H. Magidson

[57] ABSTRACT

Disclosed are adducts of 1-cyclohexene-1,2-dicarboxylic anhydride with olefins and preparation thereof by reacting an olefinically unsaturated compound and 1-cyclohexene-1,2-dicarboxylic anhydride using actinic radiation as an energy source at a temperature of from −30° C. to 150° C., preferably at from about 25° C. to 100° C. Derivatives of these compounds are useful as rust inhibitors in gasoline.

3 Claims, No Drawings

ADDUCTS OF 1-CYCLOHEXENE-1,2-DICARBOXYLIC ANHYDRIDE WITH OLEFINS

This is a division of application Ser. No. 330,154, filed Dec. 14, 1981 now U.S. Pat. No. 4,371,701.

BACKGROUND OF THE INVENTION

It is known to react 1-cyclohexene-1,2-dicarboxylic anhydride (1-CDA) thermally with conjugated dienes such as butadiene (Ber. 71B, 2199, 2280 (1938)), dimethylbutadiene and isoprene (J. Org. Chem., 23, 485 (1958)) under vigorous conditions. 1-CDA fails to react with furan, chloroprene, or cyclopentadiene at high temperatures (J. Org. Chem., 23, 485 (1958)). The imides of 1-CDA, shown to be herbicidal, as taught in U.S. Pat. No. 4,032,326, are prepared by heating the anhydride with diamines. U.S. Pat. No. 4,225,505 teaches that pyrolysis of some 1-CDA imides under extreme conditions gives pyromellitimides. It has been reported (Angew. Chem. Int. Ed. Engl., 17, 758, (1978)) that photochemical irradiation of 1-CDA in the presence of trans-stilbene gave spirooxetanes and not a 2+2 cycloadduct.

Novel dianhydrides prepared by photoaddition reactions of 1-CDA or dimethylmaleic anhydride and polyimides based upon these monomers are described by T. S. Nimry et al. in commonly assigned U.S. Ser. Nos. 294,332; 294,345; 294,347; and 294,348, filed Aug. 14, 1981, the disclosures of which are hereby incorporated by reference. In general, the photoadducts are made by irradiating the above monomers in the presence of other cyclic anhydrides and small quantities of benzophenone as sensitizer. The 1-CDA monomer is prepared by isomerization of cis-4-cyclohexene-1,2-dicarboxylic anhydride, the Diels-Alder adduct of butadiene and maleic anhydride, by heating with a few weight percent of phosphorus pentoxide ($P_2O_5$) at 200° C. (M. E. Bailey and E. O. Amstrutz, J. Am. Chem. Soc., 78, 3828 (1956)).

In reviewing these references, it is clear that irradiation of 1-CDA in the presence of olefinic and allyl compounds to form cycloadducts has not been contemplated. Neither has the art contemplated the novel bicyclooctanes prepared as photoadducts of 1-cyclohexene-1,2-dicarboxylic anhydride (1-CDA) and olefins.

The general object of this invention is to provide novel bicyclooctane compositions based upon 1-CDA and one or more olefin moieties. A more specific object of this invention is to provide photoadducts of 1-CDA and aliphatic olefins from 2-30 carbon atoms and cycloaliphatic olefins from 5-30 carbon atoms containing substituents such as halogen, cyano, nitro and alkoxy groups. Another object is to provide derivatives of the novel bicyclooctane compositions prepared by esterification and reaction with amines to form amine salts.

SUMMARY

The invention is directed to adducts of 1-cyclohexene-1,2-dicarboxylic anhydride with olefins, the amine derivatives and preparation thereof by reacting an olefinically unsaturated compound and 1-cyclohexene-1,2-dicarboxylic anhydride using actinic radiation as an energy source at a temperature of from −30° C. to 150° C., preferably at from about 25° C. to 100° C. The aliphatic amine derivative compounds are useful as rust inhibitors in gasoline.

DETAILED DESCRIPTION OF THE INVENTION

We have found that novel bicyclooctane compositions can be prepared by reacting 1-CDA with an olefinic compound or mixtures of olefinic compounds comprising olefins, diolefins and allylic compounds. 1-CDA reacts readily with olefins to form a bicyclodicarboxylic anhydride. In the novel process both aliphatic and cycloaliphatic olefins can be reacted with 1-CDA to form novel compositions.

Our process for the manufacture of the novel bicyclooctanes comprises reacting 1-CDA with an aliphatic or cycloaliphatic olefin or a mixture of aliphatic or cycloaliphatic olefins. The molecular ratio of 1-CDA to the olefin reactant can be in the range of 0.1 to 2, preferably in the range of about 0.3 to about 0.5. In a suitable method, the reaction is conducted as a batch or continuous reaction at a temperature of from about −30° to 150° C., preferably at within the range of from about 25° C. to 100° C. under nitrogen and refluxed under actinic radiation as an energy source for a period of about 1 to 100 hours, preferably in the presence of a sensitizer. In a continuous operation, the reactants are recycled continuously with means provided for an in-line distillation of a portion of the reactant mixture to obtain the bottoms as product. The overhead is returned to the reactor.

Illustrative of the olefins suitable for use in the present invention are aliphatic olefins such as ethylene, propylene, butene-1, butene-2, pentene-1, pentene-2, hexene-1, hexene-2, heptene-1, heptene-2, octene-1, octene-2, diallyl ether, decene-1, dodecene-1, tetradecene-1, octadecene-1, octyl vinyl ether, dicrotyl ether; cycloalkenes such as cyclopentene, cyclohexene, cycloheptene, cyclooctene, 1,3-cyclooctadiene, cyclopentadiene, 1,5-cyclooctadiene, and norbornene; cycloaliphatic olefins such as cyclohexylpropene, cyclohexybutene, vinylcyclohexane and 4-methyl vinylcyclohexane.

Novel bicyclooctanes of this invention can have the following structure

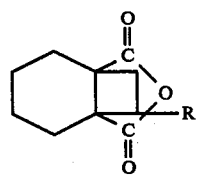

wherein R is selected from the group consisting of hydrogen, aliphatic moieties, and cycloaliphatic moieties of from 1 to 28 carbon atoms. The aforesaid moieties can be substituted with substituents selected from the group consisting of halogens, cyano, nitro and alkoxy groups. Suitable substituted aliphatic and cycloaliphatic olefins useful in the present invention are vinyl chloride, nitroethylene, butyl vinyl ether, octyl vinyl ether and allyl cyanide. The preferred aliphatic and cycloaliphatic olefins are hexene-1, octene-1, dodecene-1, cyclohexene, cycloheptene, and cyclooctene.

These structures can be

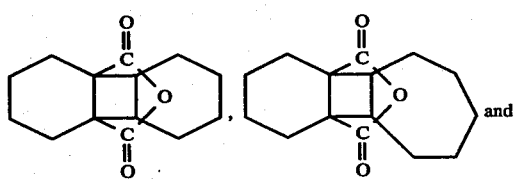

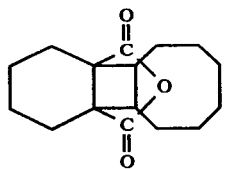

In the practice of our invention it is preferable that at least one optical sensitizer be used in conjunction with the application of actinic radiation. For purposes of our invention, the term sensitizer can be defined as being an organic compound which increases spectral response. Typical sensitizers are fluorescein derivatives, methylene blue, certain porphyrins, aromatic ketones and polycyclic aromatic hydrocarbons. For purposes of this invention, suitable sensitizers include benzophenone, Rose Bengal, methylene blue and Eosin.

Benzophenone is the preferred sensitizer at 0.1–5% by weight. Sufficient sensitizer is added to give final concentrations of 0.02 to 1% by weight in the total reaction mixture. A concentration of 0.05 to 0.25% by weight is preferred. The reaction can be run in any type of open or sealed vessel, suitably agitated. A particularly useful apparatus for the reaction when gaseous olefins such as ethylene, propylene, and the butenes are used as reagents is the Parr Pressure Reaction Apparatus, Item #3911, made by Parr Instrument Company of Moline, Illinois. This apparatus consists of a heavy-walled clear borosilicate glass bottle connected with a tank of gaseous olefin under pressure; the bottle is shaken vigorously during the reaction. Pressures of olefin of 1 to 250 psig may be used; 15 to 50 psig olefin are convenient pressures in the laboratory although, commercially, pressures over 100 psig are preferred. The reaction vessel is irradiated with ultraviolet light such as from ultraviolet lights or sunlamps of 50–500 watts, preferably mounted in reflectors with the light source about 1.5 to 3 inches from the vessel. The actinic radiation is within the range of from about 200 nanometers to about 400 nanometers or from 2000 Angstroms (Å) to 4000 Å.

The lamps used were General Electric 275 watt sunlamps. The G.E. sunlamp has 4.47 radiated watts in the ultraviolet range from 280 to 400 nanometers, and 7.03 radiated watts in the visible light range of 400 to 700 nanometers.

Reaction is continued until the calculated amount of olefin has reacted as shown by pressure drop of gaseous olefins or rise in the boiling point of refluxing mixtures; times of 1 to 100 hours may be used, depending on the nature of the olefin. Work-up generally consists of evaporating the reaction mixture at 30° C.–60° C. and 0.1–1 Torr, conveniently in a rotating RINCO evaporator (BUCHI Vacuum Rotary Evaporator ROTAVAPOR 1, Rinco Instrument Company, Inc., Greenville, Illinois).

The adduct reaction products of 1-cyclohexene-1,2-dicarboxylic anhydride and olefins can be esterified and aminated by conventional methods to prepare the mono- and diesters, and mono- and diamine salts. Alcohols useful in the esterification can contain from 1 to 18 carbon atoms and can be aliphatic, aromatic or mixtures thereof. Suitable aliphatic alcohols are methyl, ethyl, propyl, butyl, amyl, hexyl, heptyl, octyl, nonyl, decyl, dodecyl to octadecyl alcohol and mixtures thereof. Aliphatic alcohols are generally preferred for esterification because of processing ease, availability and lower costs. Suitable aromatic alcohols are benzyl alcohol, beta-phenylethanol, and para-methylbenzyl alcohol and mixtures thereof. Amines useful in the amination can contain from 1 to 18 carbon atoms and can be aliphatic, aromatic and mixtures thereof. Suitable aliphatic amines are methylamine, ethylamine, isopropyl amine, tert-butylamine, tert-octylamine, diethylamine, tributylamine, and n-octadecylamine. Suitable aromatic amines are aniline, N-methylaniline, dimethylaniline, and para-toluidine. Aliphatic amines are generally preferred for amination because of processing ease, availability and lower costs.

In order to facilitate a clear understanding of the invention, the process of preparing bicyclooctane compositions from the reaction product of an olefinically unsaturated compound and 1-CDA, the following specific embodiments are described in detail. It should be understood, however, that the detailed expositions of the application of this process, while indicating preferred embodiments, are given by way of illustration only since various charges and modifications within the spirit and scope of the invention will become apparent to those skilled in the art from this detailed description.

EXAMPLE I

A mixture of 4.56 g (30 mmole) of 1-cyclohexene-1,2-dicarboxylic anhydride (1-CDA), 75 ml (0.6 mole) of 1-hexene, and 0.2 g of benzophenone in a reaction vessel, a 250 ml Pyrex glass Erlenmeyer flask, was refluxed over a G.E. sunlamp for 18 hours. The mixture was distilled to a pot temperature of 120° C. at 200 mm to recover 70 ml of 1-hexene and leave a viscous, light yellow adduct, 7.22 g, 100 mole%, that analyzed C,71.6%; H,8.7%. Calculated for $C_{14}H_{20}O_3$: C,71.2%; H,8.5%. NMR confirmed the structure

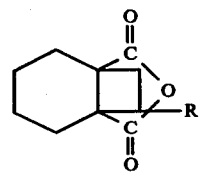

Formula I where R is n-butyl, i.e., 7-butyl bicyclo[4.2.0]octane-1,6-dicarboxylic anhydride.

EXAMPLE II

A mixture of 4.56 g (30 mmole) 1-CDA, 50 ml (0.32 mole) of 1-octene, and 0.12 g of benzophenone was treated as in Example I to yield 7.1 g (88 mole %) of the cycloadduct, 7-n-hexyl bicyclo[4.2.0]octane-1,6-dicarboxylic anhydride, Formula I, R=n-hexyl, as a viscous clear yellow oil after filtering through a little Celite.

Analysis: Calculated for $C_{16}H_{24}O_3$: C,72.7; H,9.1. Found: C,73.2; H,9.5.

EXAMPLE III

A mixture of 4.56 g (30 mmole) of 1-CDA, 22.3 ml (0.15 mole) of 1-dodecene, and 0.2 g benzophenone was reacted as in Example I to give 9.8 g (99 mole %) of photoadduct Formula I where $R=n-C_{10}H_{21}$, as a very viscous, yellow oil after it was filtered through Celite and blown with nitrogen at 100° C. to remove traces of 1-dodecene.

Analysis: Calculated for $C_{20}H_{32}O_3$: C,70.0; H,10.0. Found: C,70.5; H,10.4.

EXAMPLE IV

A mixture of 4.56 g (30 mmole) of 1-CDA, 9.58 ml (30 mmole) of 1-octadecene, 0.2 g of benzophenone, and 10 ml of dry benzene was irradiated for 20 hours by a G.E. sunlamp. The cooled solution was filtered through Celite and evaporated under $N_2$ to give 11.32 g (100 mole %) of adduct Formula I where $R=n-C_{16}H_{33}$, m.p. 55° C.-55.5° C. after crystallization from n-hexane.

Analysis: Calculated for $C_{26}H_{44}O_3$: C, 77.2; H,10.9. Found: C,77.1; H,10.9.

EXAMPLE V

A mixture of 4.56 g (30 mmole) of 1-CDA, 20 ml (0.197 mole) of cyclohexene, and 0.2 g of benzophenone was treated as in Example I to give 6.65 g of an oil that solidified on standing, 94 mole % yield. The product, perhydrobiphenylene-9, 10-dicarboxylic anhydride (Formula II) melted at 131.5° C.-133° C. after crystallization from n-heptane.

Analysis: Calculated for $C_{14}H_{18}O_3$: C,71.8; H,7.7. Found: C,71.8; H,7.7.

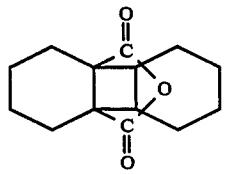

Formula II

EXAMPLE VI

A mixture of 15.0 g (99 mmole) of 1-CDA, 200 ml (1.7 mole) of cycloheptene, and 0.5 g of benzophenone was irradiated with a G.E. sunlamp for 24 hours to give 11.5 g (47 mole %) of a white solid that melted at 119° C.-121° C. after crystallization from absolute ethanol.

Analysis: Calculated for $C_{15}H_{20}O_3$:

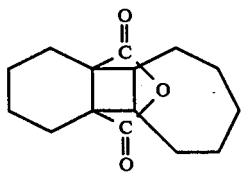

C,72.6; H,8.1; MW,248. Found: C,72.6; H,8.1; MW(VPO), 237; MW by mass spectral analysis, 249.15.

EXAMPLE VII

A mixture of 20.0 g (0.13 mmole) of 1-CDA, 200 ml (1.5 mole) of cyclooctene, and 0.5 g of benzophenone was irradiated with a G.E. sunlamp for 24 hours to give 24 g (61 mole %) of a white solid that was crystallized from absolute ethanol. It melted at 104° C.-106° C.

Analysis: Calculated for $C_{16}H_{22}O_3$:

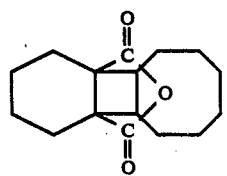

C,73.3; H,8.5; MW,262. Found: C,73.5; H,8.5; MW(VPO), 251.

EXAMPLE VIII

A mixture of 4.9 g (50 mmole) of diallyl ether, 15.2 g (0.1 mole) of 1-CDA, 0.2 g of benzophenone, and 30 ml of dry benzene was refluxed by irradiation with a G.E. sunlamp for 17 hours. The mixture was filtered through Celite and evaporated to give a hard, glassy, yellow product, 19.2 g (93 mole %).

Analysis: Calculated for $C_{22}H_{26}O_7$: C,65.7; H,6.5. Found: C,6.55; H,6.8.

$^{13}$C NMR gave these values for chemical shifts, consistent with the assigned structure

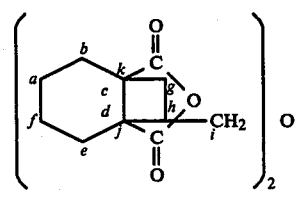

| δ tms | | | |
|---|---|---|---|
| a | 19.7 ppm | f | 20.3 |
| b | 27.1 | *g | 27.6 |
| c | 48.3 | h | 38.7 |
| d | 43.9 | i | 69.0 |
| *e | 27.6 | j | 176.4 |
| | | k | 174.2 |

*tentative assignment

EXAMPLE IX

A mixture of 14.16 g (50 mmole) of the product of Example I and 5.4 ml (50 mmole) of n-amyl alcohol was heated at 110° C. for 15 minutes and cooled to prepare the monoester. The remaining free carboxylic acid group was thereupon neutralized by the addition of 6.45 g (50 mmole) of tert-octylamine, the mixture being stirred and heated 5 minutes at 110° C., then cooled to give 20.58 (91.5 mole %) of light yellow, extremely viscous product.

Analysis: Calculated for $C_{27}H_{48}O_4N$:

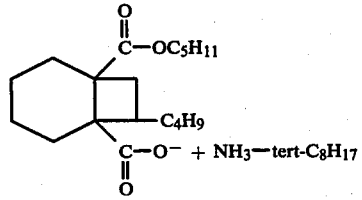

C,72.0; H,10.7; N,3.1. Found: C,71.1; H,10.5; N,3.5.

EXAMPLE X

A mixture of 14.16 g (50 mmole) of the product of Example I and 7.9 g (50 mmole) of n-decyl alcohol was reacted as in Example IX to prepare the monoester. The remaining free carboxylic acid group then reacted with 6.45 g of tert-octylamine as in Example IX to give 26.12 g (100 mole %) of light yellow, very viscous oil.

Analysis: Calculated for $C_{32}H_{58}O_4N$:

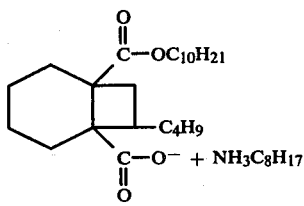

C,73.8; H,11.2; N,2.7. Found: C,73.1; H,11.5; N,2.7.

EXAMPLE XI

The effectiveness of the novel compounds of our invention as surfactants in lowering interfacial tension between solvent-extracted 5 W oil and water was measured, using a Cenco-Du Nouy Interfacial Tensiometer No. 70545 with a 6 cm platinum-iridium ring at 25° C., with double-distilled water, with these results.

| Interfacial tension | dynes/cm |
| --- | --- |
| Base oil | 41.73 |
| 1 wt % Product, Example IX | 15.91 |
| 1 wt % Product, Example X | 14.88 |

The compounds of Examples IX and X were tested as biocides and inhibitors for the growth of microorganisms by this test: 25 g of agar preparation were placed in standard Petri dishes. The agar preparation consisted of 23.5 g of Bacto Plate Count Agar, Difco Laboratories, Detroit, Mich., dissolved in 1 liter of water. Plate Count Agar contains a standard USP formula for nutrient agar consisting of:

| | |
| --- | --- |
| 5 g | Pancreatic digest of casein |
| 2.5 g | Yeast extract |
| 1 g | Glucose |
| 15 g | Agar |

Four Petri dishes were untreated and used as blanks. To the others, in duplicate, were added 2.5 ml of 1% acetone solutions of the products of Examples IX and X. All plates were uncovered for 4 hours to expose them to the spores of adventitious fungi and bacteria, then covered and stored at 30° C. for 6 days. Ratings were given at this point; 0 represents no growth; 5 shows luxuriant colonies of fungi and bacteria. Results are shown in the table.

| | Growth |
| --- | --- |
| Blank (No Additive) | 5,5 |
| Product, Example IX | 0,0 |
| Product, Example X | 0,0 |

The products of Examples IX and X were tested as rust inhibitors by the method of N.A.C.E. (National Association of Corrosion Engineers) TM-01-72, a modification of ASTM D-665. The products in 300 ml of test fuel, refinery unleaded gasoline, at the concentration of 1 lb/1000 barrels, 3.8 ppm, were kept at 100° F., a polished steel test bar added, and the fuel solution stirred 30 minutes at 100° F. Distilled water, 30 ml, was added and stirring was continued for 3.5 hours. The steel test bars were withdrawn and rated by estimating the area covered with rust, using this scale:

| A | no rust |
| --- | --- |
| B++ | 0.1% rust |
| B+ | 5% rust |
| B | 5–25% rust |
| C | 25–50% rust |
| D | 50–75% rust |
| E | 75–100% rust |

| Compound of Example | Rating |
| --- | --- |
| Blank (No Additive) | E |
| IX | B+ |
| X | B |
| Dimerized linoleic acid | B+ |

The above composition of our invention can be used in oils and solvents at concentrations of 0.01 to 10% by weight.

What is claimed is:

1. A composition of the structural formula

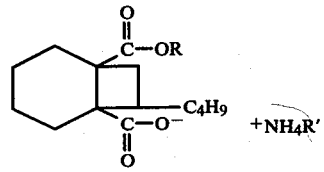

wherein R is an alkyl moiety of from 5 to 18 carbon atoms and R' is an alkyl moiety of from 8 to 18 carbon atoms.

2. The composition of claim 1 wherein R is an amyl moiety of 5 carbon atoms and R' is an octyl moiety of 8 carbon atoms.

3. The composition of claim 1 wherein R is a decyl moiety of 10 carbon atoms and R' is an octyl moiety of 8 carbon atoms.

* * * * *